United States Patent [19]
Saxton et al.

[11] Patent Number: 5,431,624
[45] Date of Patent: Jul. 11, 1995

[54] THERAPEUTIC DEVICE FOR CONTROLLING ORIENTATION OF A PATIENT'S FOOT WITH RESPECT TO THE PATIENTS LEG DURING A RECOVERY PERIOD

[76] Inventors: Loren Saxton, 11142 Promesa Dr., San Diego, Calif. 92124; Kel Bergmann, P.O. Box 8692, Rancho Santa Fe, Calif. 92067; David P. Rabuzzi, 780 West G. St., Ste. 297, San Diego, Calif. 92101; William Desouchet, 468 Santa Dominga, Solana Beach, Calif. 92075; Tony Disanto, 936 Scandia Ct., Escondido, Calif. 92025; Eddy Gosschalk, 2341 Eltingh Dr., Alpine, Calif. 91901; Kevin O'Hagan, P.O. Box 7748, San Diego, Calif. 92167; Steven Parker, 930 Via Mil Cumbres #187, Solana Beach, Calif. 92075

[21] Appl. No.: 216,453
[22] Filed: Mar. 23, 1994
[51] Int. Cl.⁶ ............................................ A61F 5/00
[52] U.S. Cl. ........................... 602/27; 602/23; 602/28; 36/89
[58] Field of Search ............ 602/5, 10, 11, 12, 14, 602/23, 27–29; 128/882; 36/89, 105, 110, 120, 121

[56] References Cited

U.S. PATENT DOCUMENTS

| | | |
|---|---|---|
| 3,548,820 | 12/1970 | Bergen . |
| 3,618,946 | 11/1971 | Lee . |
| 3,800,789 | 4/1974 | Schloss . |
| 3,955,565 | 5/1976 | Johnson, Jr. . |
| 3,976,059 | 8/1976 | Lonardo . |
| 4,088,129 | 5/1978 | DiGiulio ............... 602/23 |
| 4,217,893 | 8/1980 | Payton . |
| 4,289,122 | 9/1981 | Mason et al. . |
| 4,905,385 | 3/1990 | Perrissoud ............ 36/121 X |
| 4,980,110 | 12/1990 | Nelson et al. . |
| 5,020,523 | 6/1991 | Bodine . |
| 5,031,341 | 7/1991 | Paris et al. ............. 36/121 |
| 5,056,509 | 10/1991 | Swearington ............ 602/29 |
| 5,088,211 | 2/1992 | Walkhoff ............. 36/120 X |

FOREIGN PATENT DOCUMENTS 2004880 4/1992 WIPO ................... 602/23

OTHER PUBLICATIONS

The Century Roamer.
PRAFO–Fitting Instructions.

*Primary Examiner*—Linda C. M. Dvorak
*Attorney, Agent, or Firm*—Terry M. Gernstein

[57] ABSTRACT

A therapeutic device includes an ankle-controlling section slidably attached to a foot-supporting section. Sliding the ankle-controlling section with respect to the foot-supporting section changes the angle between the two sections to flex a wearer's foot in a desired manner. The device includes a plurality of soles which are spaced from the user's heel to prevent ulceration of the heel, and a swing arm outrigger that is pendently supported on the ankle-controlling section as well as at least one replaceable liner. A template is located on the ankle-controlling section so exact angles can be set and recorded.

16 Claims, 7 Drawing Sheets

THERAPEUTIC DEVICE FOR CONTROLLING ORIENTATION OF A PATIENT'S FOOT WITH RESPECT TO THE PATIENTS LEG DURING A RECOVERY PERIOD

TECHNICAL FIELD OF THE INVENTION

The present invention relates to the general art of therapeutic devices, and to the particular field of therapeutic devices for controlling a patient's foot position during a period of recuperation or rehabilitation.

BACKGROUND OF THE INVENTION

Many medical procedures require a recuperation period during which a patient is immobile in a supine position. It has been found that many patients are susceptible to a variety of problems during such recovery time. Such problems as leg misalignment, foot droop, and heel sores are often encountered in patients who have been bedridden for some time.

Accordingly, the art has included a variety of therapeutic splint devices for maintaining a fixed position or a fixed orientation of a patient's foot and/or leg during recovery. These devices include means for controlling the amount of flex permitted as well as means for preventing hip rotation. Some devices also include means for preventing contact between a patient's heel and the device.

However, while several of these devices attempt to control flexing of the patient's ankle, precise and identifiable control is not fully exercised. For example, some devices use a metal plate that is bent to hold a patient's foot in a pre-set orientation. While the foot can be held in a pre-set orientation, such orientation is not precisely set and cannot be accurately recorded whereby results from one procedure are not fully available for reference in future procedures. Still further, such devices generally are not amenable for use when the patient begins walking as they will not support the patient's weight and still retain the pre-set flex of the patient's ankle.

Therefore, there is a need for a therapeutic device for controlling orientation of a patient's foot with respect to the patient's leg during a recovery period in a precise and repeatable manner, even if the device must support the patient's weight for some period of time.

Several devices also prevent undesired hip rotation during the recovery period using an outrigger arm mounted on the device. However, such arms may interfere with ambulation of a patient if the device is worn during such ambulation. Therefore, there is a need for a therapeutic device for controlling orientation of a patient's foot with respect to the patient's leg during a recovery period in which hip rotation can be controlled in a manner that is not likely to interfere with a patient's walking with the device attached to his or her foot.

With further regard to the ambulation of a patient, if a patient having a foot controlling device in place wishes to walk about, he or she must often remove the device because it cannot bear the burdens associated with a patient's weight, or does not lend itself to avoiding certain particular problems that are encountered by such a patient as he or she initially begins to walk after a period of inactivity. In this manner, some such devices actually discourage a patient from walking during the recovery period. Therefore, there is a need for a therapeutic device for controlling orientation of a patient's foot with respect to the patient's leg during a recovery period which can be used when a patient walks and can actually encourage such walking.

Still further, some treatments requiring a foot control device also require a knee brace. Therefore, to fully co-ordinate such treatments, the foot-controlling device should accommodate the knee brace. Accordingly, there is a need for a therapeutic device for controlling orientation of a patient's foot with respect to the patient's leg during a recovery period which can accommodate a knee brace.

OBJECTS OF THE INVENTION

It is a main object of the present invention to provide a therapeutic device for controlling orientation of a patient's foot with respect to the patient's leg during a recovery period.

It is another object of the present invention to provide a therapeutic device for controlling orientation of a patient's foot with respect to the patient's leg during a recovery period in a precise and repeatable manner.

It is another object of the present invention to provide a therapeutic device for controlling orientation of a patient's foot with respect to the patient's leg during a recovery period in a precise and repeatable manner, and will retain the precisely set orientation while supporting the patient's weight.

It is another object of the present invention to provide a therapeutic device for controlling orientation of a patient's foot with respect to the patient's leg during a recovery period and which can be worn while the patient walks.

It is another object of the present invention to provide a therapeutic device for controlling orientation of a patient's foot with respect to the patient's leg during a recovery period in which hip rotation can be controlled in a manner that is not likely to interfere with a patient's walking with the device in place on his or her foot.

It is another object of the present invention to provide a therapeutic device for controlling orientation of a patient's foot with respect to the patient's leg during a recovery period and which can accommodate a knee brace.

SUMMARY OF THE INVENTION

These, and other, objects are achieved by a therapeutic device for controlling orientation of a patient's foot with respect to the patient's leg during a recovery period having an ankle-controlling section slidably connected to a foot-supporting section, with movement of the ankle support relative to the foot support altering the angle between these two sections. A template is included so the exact angle can be set, read and recorded. The sliding connection can be changed to precisely and repeatably set the angle whereby precision and accuracy are included in this portion of a therapeutic procedure. The device is formed of plastic and will retain a set orientation even if the patient places his or her weight on the device. A swing arm outrigger is pendently supported on the ankle-controlling section so its natural condition is out of the way and it will extend transversely only when desired.

The therapeutic device of the present invention further includes a slot means for accommodating a knee bracing element as well as means for accommodating a walking sole so the device can be used in conjunction with other forms of therapy as well.

More specifically, the device is a molded plastic foot skin protector which positions a patient in a desired anatomical alignment, and which can be adjusted to accommodate contracture of the ankle. The device eliminates pressure to existing heel sores and will help prevent decubitus pressure sores. Plastic is molded around the patient's posterior calf and the planter aspect of the foot to hold the foot in dorsiflexion. The device also includes a soft padded liner, and can include a non-skid walking sole. The device can be prefabricated, and can be used for either the right or the left leg and can include hook and loop fasteners to attach the device to the patient. The patient's heel is suspended in air thereby relieving all pressure on that heel.

After the device is applied to a patient's leg, it holds the patient's lower extremity in proper anatomical position while suspending the posterior of the heel in mid air within the device. It can be used as a limited ambulation device, and can extend beyond the patient's toe.

DETAILED DESCRIPTION OF THE PREFERRED EMBODIMENT OF THE INVENTION

Figure 1:
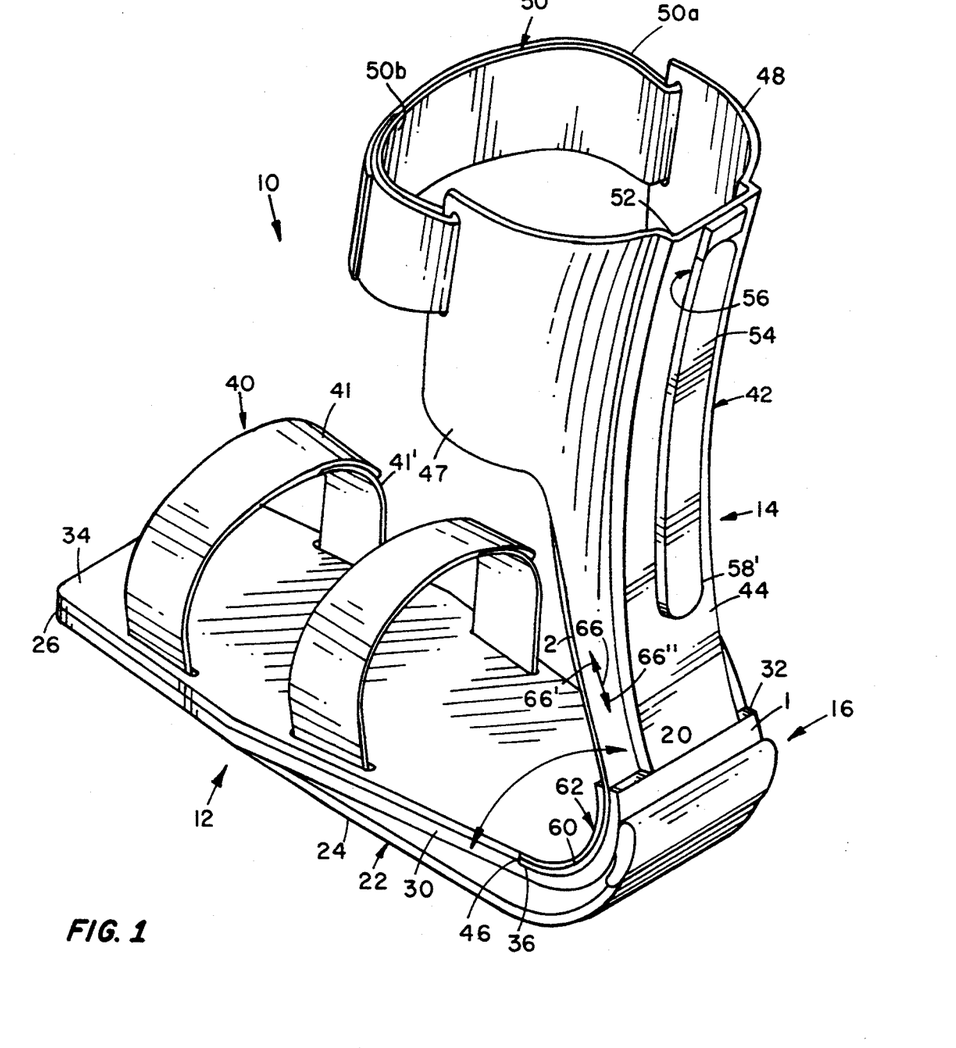
FIG. 1 is a rear perspective view of a therapeutic device for controlling orientation of a patient's foot with respect to the patient's leg during a recovery period embodying the present invention.
Figures 11, 12:
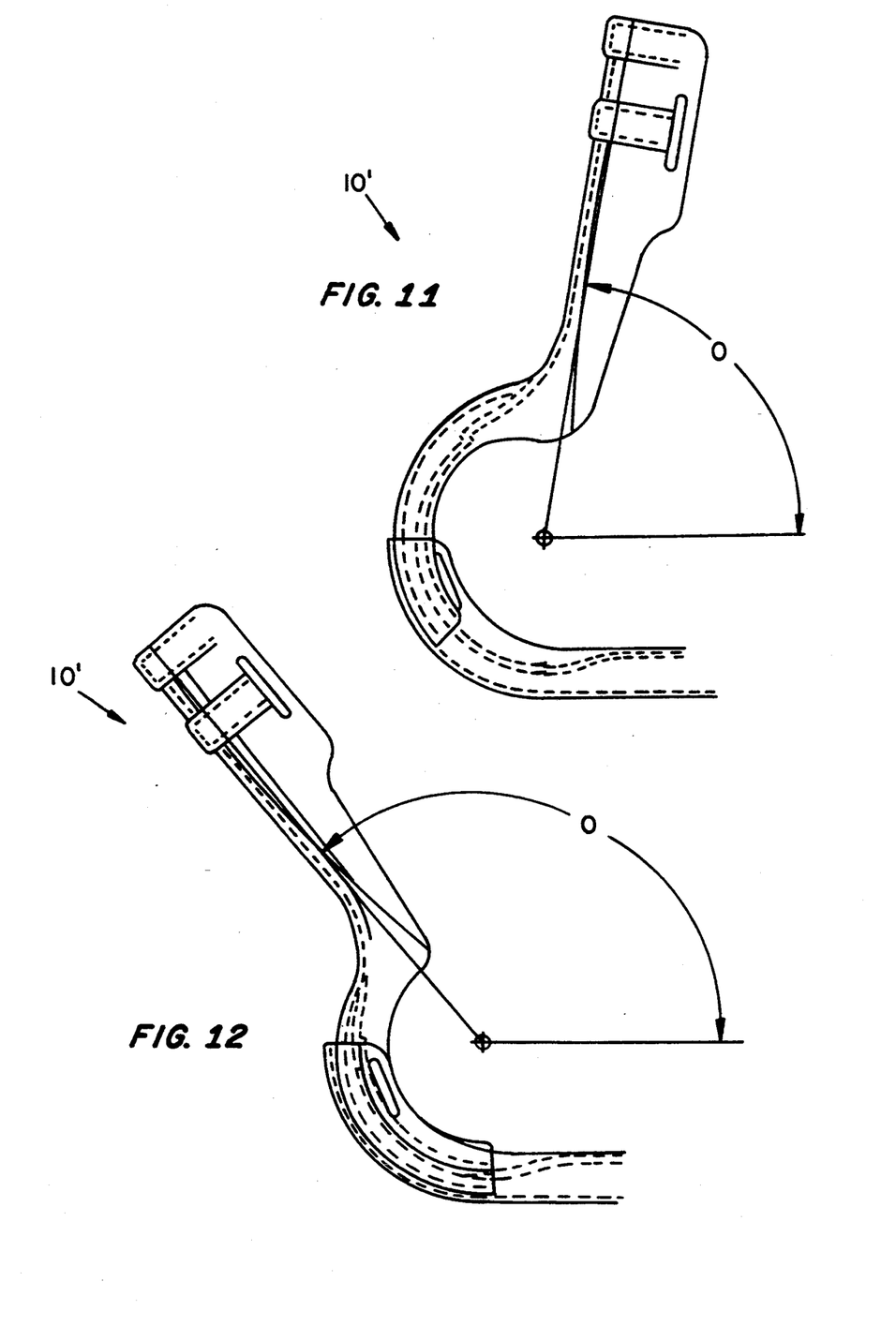
FIG. 11 shows the second form of the device with the ankle-controlling section in one orientation with respect to the foot-supporting section.
FIG. 12 shows the second form of the device with the ankle-controlling section in a second orientation with respect to the foot-supporting section.

Shown in FIG. 1 is a therapeutic device 10 for controlling orientation of a patient's foot with respect to the patient's leg during a recovery period embodying the present invention. The device is preferably formed of plastic and includes a foot-supporting section 12 slidably attached to an ankle-controlling section 14 by an attaching means 16. Ankle-supporting section 14 is shown in FIG. 1 in a first orientation which defines approximately a 90° angle between these two sections, but can be moved, as will be understood from the ensuing discussion, by sliding section 14 with respect to section 12 so the angle between these two sections, represented in FIG. 1 by $\theta$, decreases. As will be understood by those skilled in the art, changing angle $\theta$ flexes the patient's foot. Marks 20 on section 14 define a template and are used to set the angle $\theta$ and are calibrated accordingly whereby this angle can be accurately, precisely and repeatably set for each procedure. The angle can also be recorded for future reference for other procedures. Reference can be made to FIGS. 11 and 12 which show the effects of this sliding movement of section 14 relative to section 12 for a second form of the device.

Figures 2, 3:
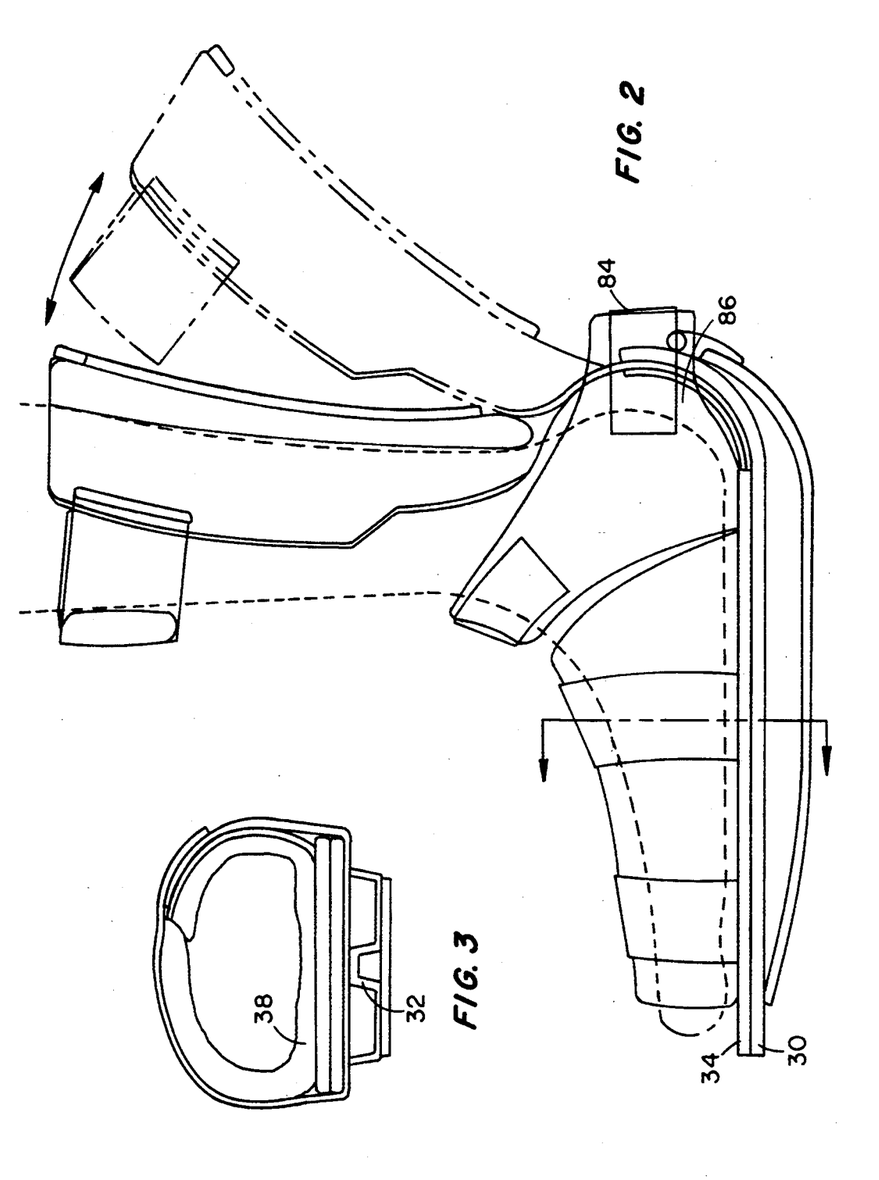
FIG. 2 is a side elevational view thereof, with one orientation of the ankle-controlling section relative to the foot-supporting section being shown in solid lines and a second orientation being shown in dotted lines.
FIG. 3 is an elevational view along line 3—3 of FIG. 2.
Figures 4, 5:
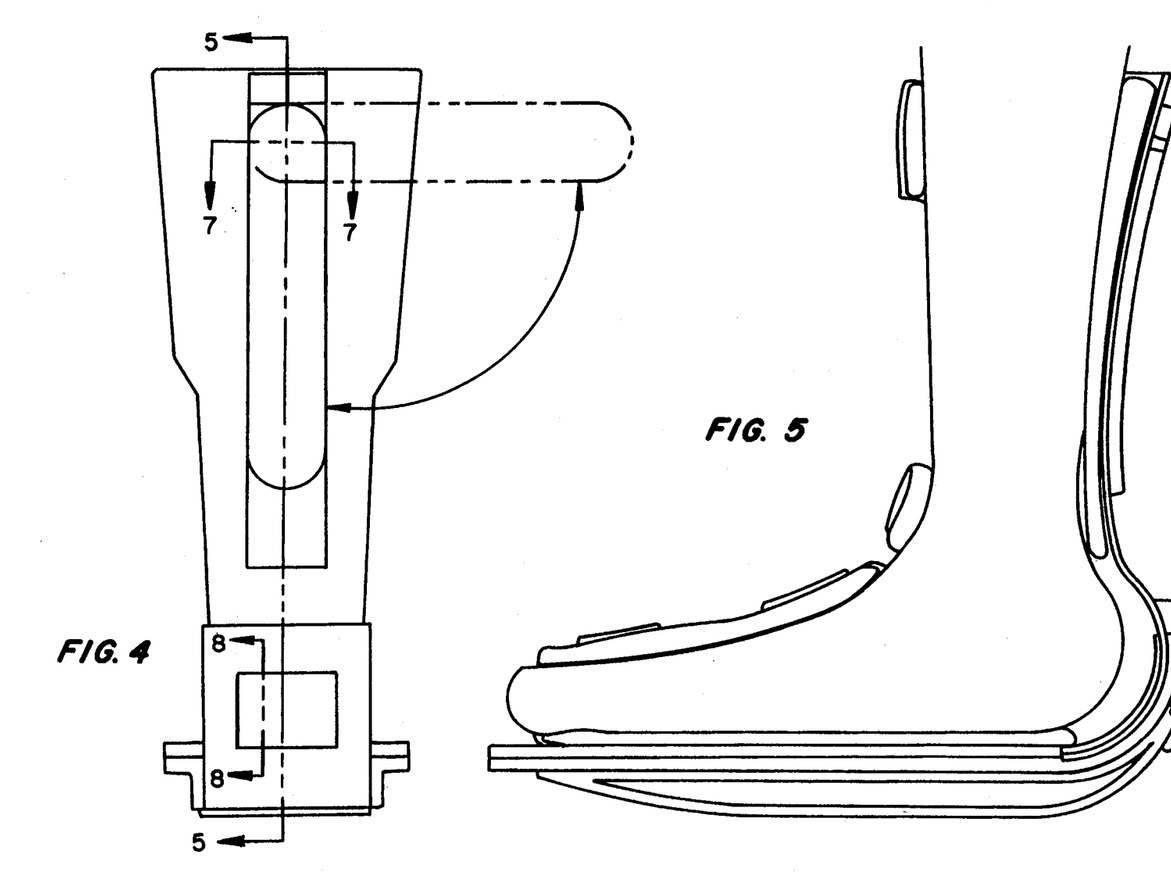
FIG. 4 is a rear elevational view of the device with a storage orientation of the swing arm outrigger being shown in solid lines and an in-use orientation thereof being shown in dotted lines.
FIG. 5 is a side elevational view taken along line 5—5 of FIG. 4.
Figure 6:
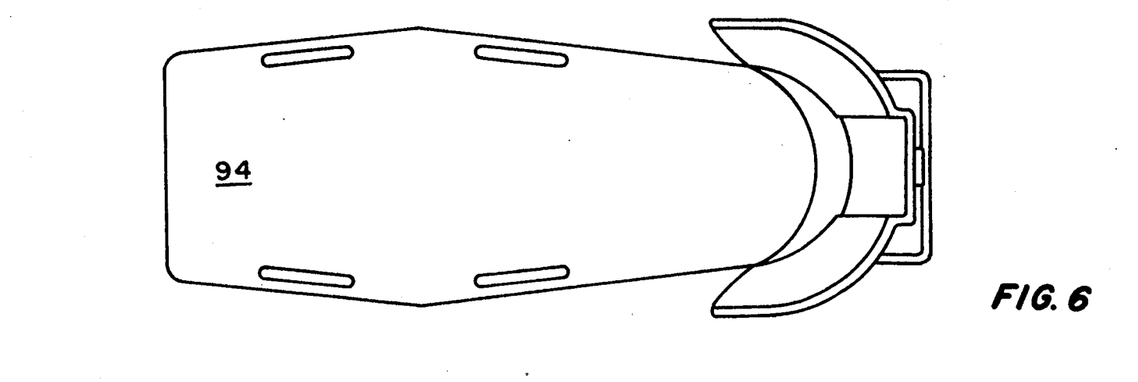
FIG. 6 is a top plan view of the device.

More specifically, foot-supporting section 12 of device 10 includes a ground-engaging sole 22 having a non-slip surface 24 engaging the ground and which extends from toe tip 26 of the device adjacent to attaching means 16. Sole 22 can be arcuate as shown in FIG. 2 or it can be planar as shown in FIG. 1 or some other shape as desired. The sole 22 is fixed to a midsole 30 at opposite ends of the sole 22 and is supported therebetween by a support structure 32, best shown in FIG. 3. Support structure 32 can include honeycomb supports or simply include a U-shaped channel 33 that extends longitudinally of the sole as shown in FIG. 3. Midsole 30 is formed of hard plastic, and extends from toe tip 26 past attaching means 16. As will be understood from the following disclosure, attaching means 16 is fixedly mounted on midsole 30 adjacent to aft end 32 of midsole 30. An insole 34 is fixed to midsole 30 and extends from toe tip 26 to an aft shoulder 36 located to be beneath a user's heel when that user is wearing device 10.

A foam liner 38 (shown in FIG. 3) is removably placed on the insole to be located between a user's foot and the insole. The liner can be removed and replaced as necessary. A plurality of straps, such as straps 40, releasably attach the device to the user's foot. The straps can include overlapping strap pieces 41 and 41' that are connected together by releasable coupling means, such as VELCRO or the like whereby the size thereof can be adjusted. There are two straps 40 shown in FIG. 1, however, more than two straps can be used without departing from the scope of the present invention. For example, a third strap can be located near attaching means 16 if suitable.

Ankle-controlling section 14 includes a body 42 that is shaped and sized to closely fit onto the posterior calf portion of a user. As shown, body 42 includes a neck portion 44 that extends from forward edge 46 to a trunk portion 47 that fits against the user's calf. Trunk portion 47 extends from neck portion 44 to a top rim 48, with a leg-attaching strap 50 fixed to trunk portion 46 adjacent to top rim 48. Strap 50, like straps 40, includes two overlapping strap pieces 50a and 50b that are releasably attached to each other by VELCRO or the like whereby the straps can be adjusted to fit the user.

A slot 52 is defined in ankle-controlling section 14 to extend longitudinally thereof from rim 48 towards edge 46 and is sized to slidably accommodate a portion of a knee brace. This allows device 10 to be used in connection with a knee brace without detracting from any therapy associated with either device. Since the knee brace, per se, is not part of the present invention, no such element is shown.

Figure 7:
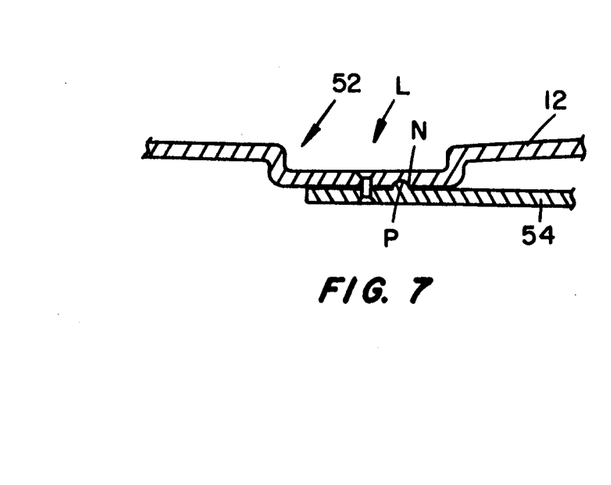
FIG. 7 is a view taken along line 7—7 of FIG. 4.
Figure 13:
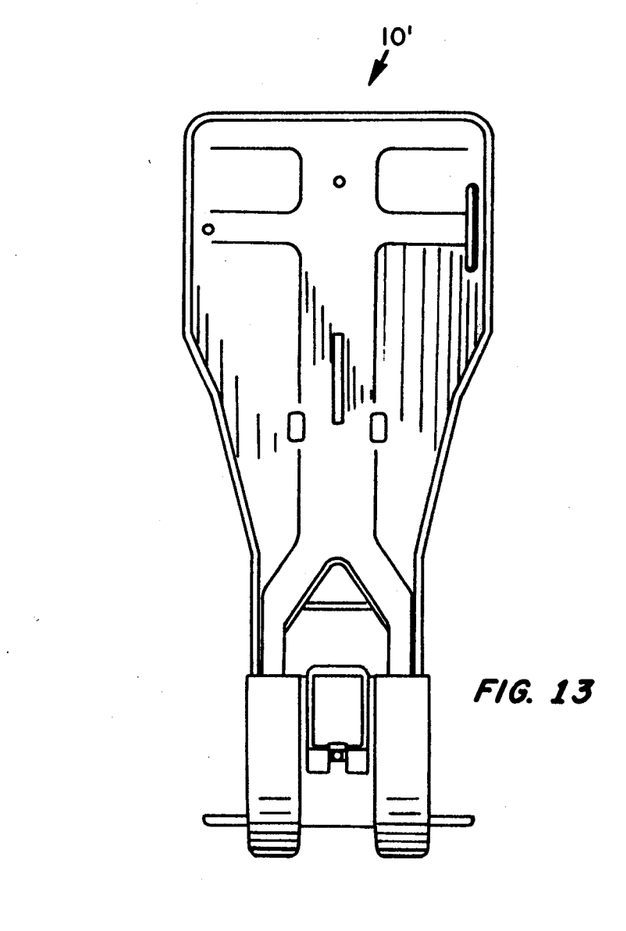
FIG. 13 is a rear elevational view of the second form with the swing arm outrigger extended into an orientation to prevent hip rotation.
Figure 14:
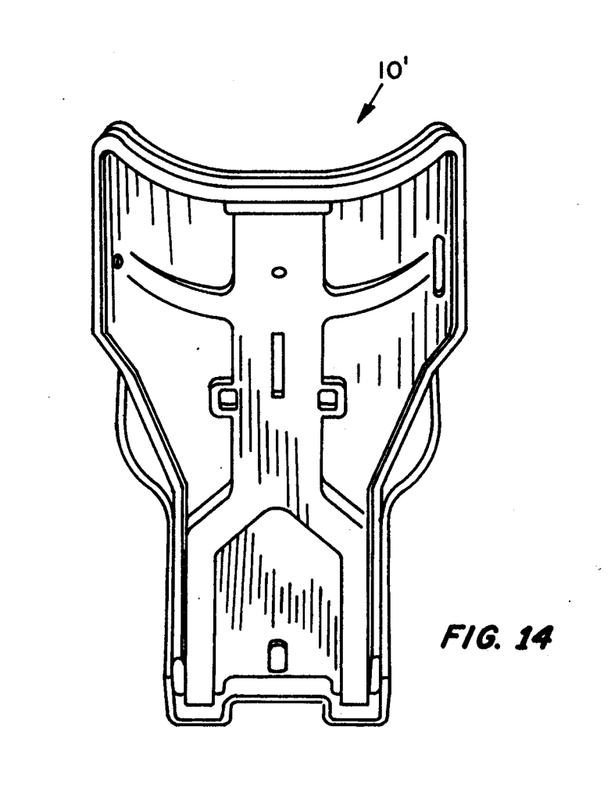
FIG. 14 shows the second form of the device with the ankle-controlling section separated from the foot-supporting section.

Also attached to ankle-controlling section 14 is a swing arm outrigger 54. Outrigger 54 is used to control hip rotation, and is pendently attached to trunk 47 at top end 56 of outrigger 54 with bottom end 58 free. Outrigger 54 pivots about end 56 from the storage position shown in FIG. 1 to a use position shown in FIG. 13. Since the outrigger arm is supported at the top thereof, it will tend to move into the FIG. 1 position unless it is deliberately moved. In this manner, the arm will tend to move out of the way if left unattended and device 10 is in a vertical orientation such as shown in FIG. 1. This prevents arm 54 from getting in the way if the patient is attempting to walk with device 10 on their foot. In order to ensure that the swing arm remains in an extended (FIG. 7) position, releasable lock L includes a notch N is defined in trunk 42 and a resilient projection P on arm 54 is releasably received in that notch when the arm is in the extended orientation. The projection will move out of the notch when the arm is moved towards the storage position (FIG. 1).

Turning now to the specific means for adjusting angle $\theta$, and referring to FIGS. 1 and 2, it can be seen that neck 44 includes a curved section 60, that will be referred to herein as the contour section. Contour section 60 is a portion of a circle, and is slidably received in a correspondingly curved section 62 of the foot-supporting section, with section 62 being a slot defined between midsole 30 and insole 34. As can be understood from FIG. 1, angle $\theta$ is set by the location of contour section 60 in relation to curved section 62. Neck 44 is formed of hard material, such as plastic, or the like, and thus will tend to retain an orientation relative to foot-supporting section 12 once contour section 60 is slid into the slot between insole 34 and midsole 26, and fixed at that position by attaching means 16. Double-headed arrow 66 indicates the movement of ankle-controlling section 14, with direction 66' indicating dorsiflexion and direction 66" indicating plantar flexion.

Figure 8:
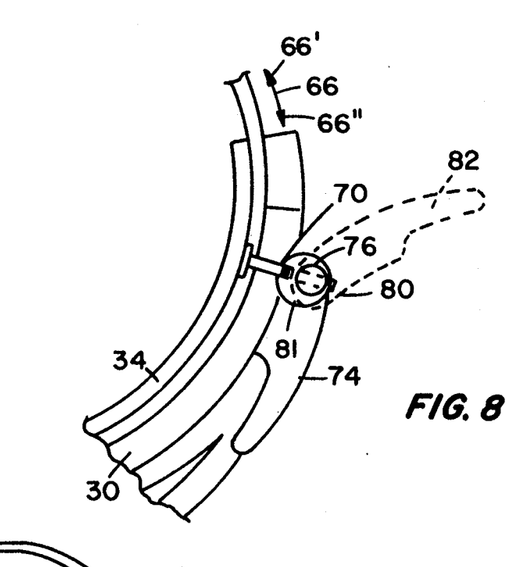
FIG. 8 is a view taken along line 8—8 of FIG. 4.

Attaching means 16 fixes ankle-supporting section 14 to foot-supporting section 12 when the desired orientation of those two sections is established. Attaching means 16 is shown in FIGS. 1, 2 and 8, and includes a bolt 70 attached at its head 72 to insole 34, and having a cam handle 74 attached to a threaded end 76 adjacent to midsole 30. Bolt 70 is fixed to midsole 30 and to insole 34, but is received through a slot defined through contour 60 of neck portion 44 so ankle-controlling section 14 can be moved relative to foot-supporting section 12. Cam handle 74 is pivotally attached to bolt 70 to move between a locking position shown in full lines in FIG. 8 in which the ankle-controlling section is locked to the foot-supporting section, and an unlocking position shown in dotted lines in FIG. 8 in which the ankle-controlling section is free to slidably move relative to the foot-supporting section. In the locking position, cam handle 74 engages the aft end of ground-engaging section 22 to further support that section should the user desire to walk with device 10 in place on their foot. The user will not walk when the ankle-controlling section is free from the foot-supporting section, thus the cam handle can move away from the ground-engaging section when in the unlocking position. Cam handle 74 includes a cam 80 on the end thereof that engages a compliant washer 81 located between cam 80 and midsole 30 and includes a hand-grasped segment 82 on the other end thereof. Movement of the cam handle from the unlocked position into the locked position rotates cam 80 into engagement with washer 81, which is flexible enough to permit the cam to move over center, yet will jam against the midsole tightly against contour 60. The jamming force created by cam 80 is sufficient to hold contour 60 in place so it will no longer slide relative to the foot-supporting section. This will hold the ankle-controlling section in place with the set angle $\theta$ whereby the desired flex is established and held by device 10. If desired, a strap 84 can be attached to the device adjacent to cam lever 74 to close over that cam lever and further ensure that the lever will not release in an inadvertent and undesired manner.

As will be understood from FIG. 2, contour section 60 is sized, shaped and located to space insole 34 from a user's heel when device 10 is in place on the user's foot. This space is indicated in FIG. 2 at 86. Space 86 prevents decubitus pressure sores.

Figure 9:
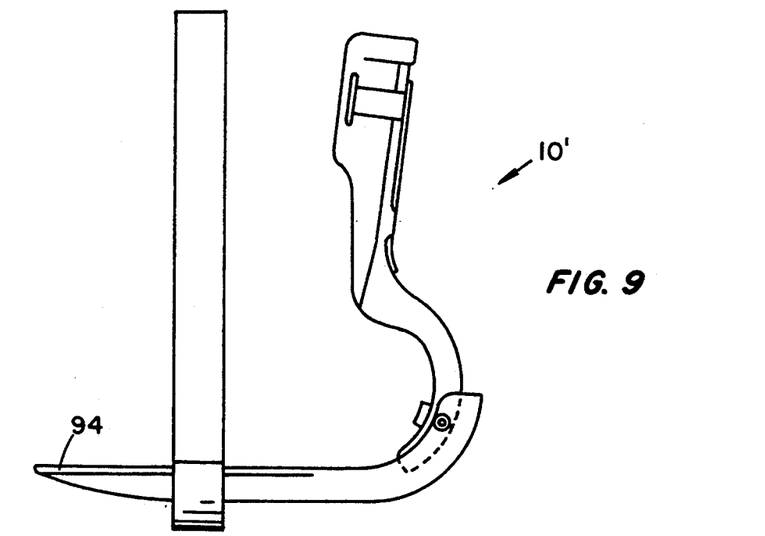
FIG. 9 is a side elevational view of a second form of the device.
Figure 10:
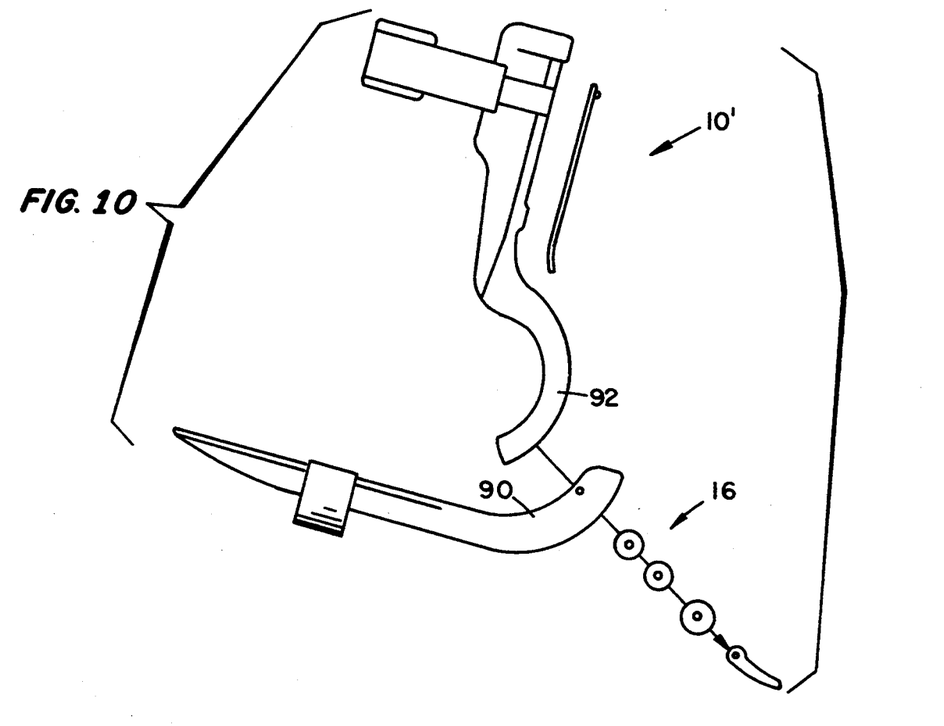
FIG. 10 is an exploded perspective view of the second form.

A second form of the device is shown in FIGS. 9 and 10 as device 10'. Device 10' is similar to device 10 except that device 10' includes two slot defining-channels 90 on the foot-supporting section, and two rails 92 on the ankle-controlling section. Rails 92 are slidably received in channels 90, and attaching means 16 is located between the slot-defining channels. Further non-slip treads can be fixed to the outer surface of the foot-supporting section on the channels 90.

It is noted that the insole includes a top surface 94 that is free of any rivets, screws or other irregularities so no rubbing occurs against a user's foot. The foot-supporting portion is also sized to extend forward of a user's foot to keep sheets and blankets off the user's toes when the device is worn in bed.

It is understood that while certain forms of the present invention have been illustrated and described herein, it is not to be limited to the specific forms or arrangements of parts described and shown.

We claim:

1. A therapeutic device for controlling orientation of a patient's foot with respect to the patient's leg during a recovery period comprising:
   A) a foot-supporting section which includes
      (1) a ground-engaging sole,
      (2) a midsole on said ground-engaging sole,
      (3) an insole on said midsole, and
      (4) means for attaching a user's foot to said foot-supporting section;
   B) an ankle-controlling section which includes
      (1) a body adapted to be positioned posteriorly to the user's leg,
      (2) means for attaching a user's leg to said body, and
      (3) an arcuate contour section; and
   C) attaching means for attaching said ankle-controlling section to said foot-supporting section which includes
      (1) means on said foot-supporting section for slidably receiving said contour section, wherein the angle between said body of said ankle-controlling section and said foot-supporting section is changed by sliding said arcuate contour section relative to said foot-supporting section, and
      (2) clamp means for clamping said contour section to said foot-supporting section.

2. The therapeutic device defined in claim 1 further including a swing arm outrigger having one end pivotally supported on said body, and having another end free.

3. The therapeutic device defined in claim 2 further including a lock means on said outrigger for locking said outrigger in a position extending transversely outward from said body.

4. The therapeutic device defined in claim 3 wherein said lock includes a notch defined in said body and a projection on said outrigger.

5. The therapeutic device defined in claim 1 further including a liner on said insole.

6. The therapeutic device defined in claim 1 further including an adaptor slot means on said body for accommodating a knee brace on the user.

7. The therapeutic device defined in claim 1 wherein said ground-engaging sole includes a non-slip surface.

8. The therapeutic device defined in claim 7 wherein said ground-engaging sole is arcuate.

9. The therapeutic device defined in claim 1 wherein said ground-engaging sole abuts said clamp means.

10. The therapeutic device defined in claim 1 wherein said means for attaching said foot-supporting section to a user's foot includes a plurality of straps.

11. The therapeutic device defined in claim 1 wherein said contour section has a shape adapted to be spaced from a user's foot when the device is in place on the user's foot.

12. The therapeutic device defined in claim 1 wherein said midsole includes a shoulder against which an end edge of said body abuts when said ankle-controlling section is in a first orientation with respect to said foot-supporting section, said end edge is spaced from said shoulder when said ankle-controlling section is in a second orientation.

13. The therapeutic device defined in claim 1 further including a support structure between said ground-engaging sole and said midsole.

14. The therapeutic device defined in claim 1 wherein said means for slidably receiving said contour section includes a slot-defining element on said foot-supporting section and a rail on said ankle-controlling section.

15. The therapeutic device defined in claim 1 wherein said clamp means includes a cam lever having a cam on one end thereof, a fastener means for fastening said cam lever to said insole, said fastener means engaging said cam lever at said cam, said cam being located to engage said midsole when said clamp means is locked, said contour section being located between said insole and said midsole, and including a slot through which a bolt extends.

16. The therapeutic device defined in claim 1 wherein said clamp means includes a compliant washer adjacent to said midsole.

* * * * *